United States Patent
Dai et al.

(10) Patent No.: US 9,139,488 B2
(45) Date of Patent: Sep. 22, 2015

(54) SUBLIMATION METHOD FOR THE PURIFICATION OF ORGANIC SMALL MOLECULES

(75) Inventors: Lei Dai, Beijing (CN); Lifei Cai, Beijing (CN)

(73) Assignees: GUANGDONG AGLAIA OPTOELECTRONIC MATERIALS CO., LTD., Guangdong (CN); BEIJING AGLAIA TECHNOLOGY DEVELOPMENT CO., LTD., Beijing (CN)

( * ) Notice: Subject to any disclaimer, the term of this patent is extended or adjusted under 35 U.S.C. 154(b) by 0 days.

(21) Appl. No.: 14/238,825

(22) PCT Filed: Aug. 3, 2012

(86) PCT No.: PCT/CN2012/079636
§ 371 (c)(1),
(2), (4) Date: Feb. 13, 2014

(87) PCT Pub. No.: WO2013/023533
PCT Pub. Date: Feb. 21, 2013

(65) Prior Publication Data
US 2014/0191422 A1  Jul. 10, 2014

(30) Foreign Application Priority Data

Aug. 13, 2011 (CN) .......................... 2011 1 0233398

(51) Int. Cl.
| | |
|---|---|
| *B01D 7/00* | (2006.01) |
| *C07B 63/00* | (2006.01) |
| *H01L 51/00* | (2006.01) |
| *B01D 7/02* | (2006.01) |
| *H01L 51/56* | (2006.01) |

(52) U.S. Cl.
CPC . *C07B 63/00* (2013.01); *B01D 7/00* (2013.01); *B01D 7/02* (2013.01); *H01L 51/0025* (2013.01); *H01L 51/56* (2013.01)

(58) Field of Classification Search
CPC .............................. C07B 59/002; B01D 15/10
USPC ................... 422/244, 243, 251, 260; 556/466
See application file for complete search history.

(56) References Cited

U.S. PATENT DOCUMENTS

2004/0211038 A1   10/2004   Chang et al.

FOREIGN PATENT DOCUMENTS

| CN | 1548499 A | 11/2004 | |
|---|---|---|---|
| CN | 1714061 A | 12/2005 | |
| CN | 101310812 A | 11/2008 | |
| JP | 2005-313069 A | 11/2005 | |
| JP | 2007-044592 A | 11/2007 | |
| KR | 2002-0088928 A | 11/2002 | |
| TW | 200934576 A | 8/2009 | |
| WO | 03051796 A1 | 6/2003 | |
| WO | WO03/051796 A1 * | 6/2003 | .............. C07B 63/00 |

* cited by examiner

*Primary Examiner* — Sudhakar Katakam
*Assistant Examiner* — Pancham Bakshi
(74) *Attorney, Agent, or Firm* — Maschoff Brennan

(57) ABSTRACT

Disclosed is an improved sublimation method for the purification of organic small molecules. The new method features that barriers are applied in the collection region of sublimation tube so that the gas flow path is modified to pass through or bypass the barriers from the heating region to the vacuum pump. The arrangement of the barriers can effectively separate the main product from the impurities. The main product is enriched in a collection region, while the volatile impurities are enriched in an impurity region. This method has been proved to improve the quality of sublimed materials substantially according to the purity measurements and OLED performance tests.

20 Claims, 6 Drawing Sheets

SUBLIMATION METHOD FOR THE PURIFICATION OF ORGANIC SMALL MOLECULES

TECHNICAL FIELD

The present invention relates to the field of organic compounds, in particular to the purification of organic small molecules, i.e. an improved sublimation method.

BACKGROUND

Over the past few decades, tremendous progresses have been made in the field of organic electronic devices, e.g. OLEDs (Organic Light Emitting Diodes), OTFTs (Organic Thin Film Transistors), OPVs (Organic Photovoltaics) and the like; especially for OLED materials, they have been recognized worldwide as being applicable to the next generation of novel flat-panel display technology due to their advantages, such as spontaneous optical rotation, high contrast, high response rate, wide angle of view, low power consumption, full color, simple fabrication process, etc. Thus in recent years, these OLED materials have drawn great attention from acedemic and industry.

Fast progresses have been made in the application and industrialization of OLED materials since Qingyun Deng and Van Slyke from Kodak began their groundbreaking work on OLED materials. Among those factors that affect the performances of OLED devices, the purity of OLED materials is one of the most important, which has a direct impact upon not only the performances but also the reliability of the devices. In fact, the purity of an OLED material has a direct impact upon the charge (electron and hole) transport capacity, so it is a key aspect to examine for satisfying performance of an organic electronic device. In terms of technology, OLED materials are currently divided into two main categories: small-molecular organic materials and high-molecular materials. Among the commercially available materials so far, the small-molecular OLED organic materials are employed by most of the companies. At present, there are several main purification processes for the acquisition of high-purity small-molecular organic materials, e.g. zonal melting process, chromatogram comparison process, in-situ filtration technique, temperature gradient sublimation separation process and so on. Among these processes, the temperature gradient sublimation separation technique is the most useful and common purification method for organic semiconductor small-molecular materials, because there is no liquid-phase state in most of the organic small-molecular substances at atmospheric pressure or low pressure. At present, this technique is being used by a large number of OLED material researchers and manufacturers for the production of highly pure organic small molecular OLED materials. The mechanism of this process relies on a temperature gradient, which is built up by stepwise heating of the sublimation tube, allowing the main product and impurities with different sublimability to condense seperately. This process is shown in FIG. 1.

During heating in the heating region 1 as shown in FIG. 1, the pure product is enriched on the inner wall of the tube in the collection region 2 (a heating region with a set particular temperature), in the presence or absence of an inert gas flow, while more volatile impurities are delivered and deposited in the impurity region 3, which has a certain distance away from the product, and the involatile impurities remain in the sample boat. This conventional approach is simple, however, a single time of sublimation typically fails to meet the purity requirement and the product needs to be sublimed for a second time or even more times to reach sufficiently high purity, thus the entire purification procedure is quite time-consuming and material-consuming. It is therefore necessary to improve the sublimation purification method for obtaining highly pure materials, and eventually high-efficiency and low-cost devices.

SUMMARY OF THE INVENTION

Given the shortcomings in the arts above, provided in the present invention is an improved sublimation purification method of organic small molecules, in which the movement path of a to-be-sublimed substance is modified by means of internal space obstruction, to achieve better separation between the main product and the impurities in the process of sublimation, and therefore higher sublimation yield.

The sublimation purification method of organic small molecules comprises the following steps: an organic-small-molecule compound to be sublimed is placed in the heating region of a sublimation tube; the vacuum pump is turned on; the heating is applied stepwise and the necessary temperature gradient is built, then the mail product is enriched in a collection region and volatile impurities are enriched in an impurity region. This new method features that barriers are fastened in the collection region so that gas is capable of passing through or bypassing the barriers from the heating region to the vacuum pump.

Barriers may also be fastened in the impurity region.

The barriers may be staggered semicircular plates and crosswise fastened on the inner wall of the collection region.

The barriers may be circular plates with a plurality of through holes, the collection region and/or the impurity region is composed of a plurality of hollow circular cylinders aligned and in close contact with the inner wall of the sublimation tube, a circular plate is fastened in each of the circular cylinder, a particular angle is formed between the axial direction of the circular cylinder and the plane of the circular plate, and the circular cylinder and the circular plate form a space obstruction unit.

The axial direction of the circular cylinder is perpendicular to the plane of the circular plate.

The through holes are uniformly distributed on the circular plate.

The conventional sublimation tubes are closing systems with one end being connected to a vacuum pump, and the other end being closed or equiped with a gas inlet. The sublimation tube is divided into the heating region, the collection region and the impurity region in the order of a decreasing distance from the pump. In the collection region and the impurity region, there are several short inner tubes connected to each other and in close contact with the outer tube. The short inner tubes can be taken out to collect the product and impurities seperately. In the present invention, a plurality of barriers are placed in the collection region to form a zig-zagged path for the sublimed substance to pass through, which allows a better seperation of the main product from the more volatile impurity, leading to increased purity of the collected product. Meanwhile, the presence of these barriers results in smaller loss of material that is directly pump away. Similarly, barriers can also be fastened in the collection region to further improve the effect described above.

The barriers may be in a semicircular shape. Sublimed gas is capable of bypassing the semicircular edges because the neighboring semicircular plates are staggered. The main product and the impurities will be deposited on the semicircular plates or the inner walls at the collection region and the impurity region, respectively. The semicircular plates may be designed to be detachable to facilitate the collection of the main product or the impurities.

In the present invention, for further convenience of collecting the product or the impurities, the collection region and/or the impurity region contains small circular cylinders connected one after another. Each cylinder has a circular plate with through holes. The circular cylinder and the circular plate form a space obstruction unit. Therefore, the collection region and the impurity region are composed of several such aligning units, through which the sublimed gas can pass via the holes on the plates. These small circular cylinders can be taken out to facilitate the collection.

Experiments have proved that the method of this invention is advantageous in the seperation of the product from the impurities, increasing the product's purity and reducing its loss.

DETAILED DESCRIPTION OF THE EMBODIMENTS

Figure 1:
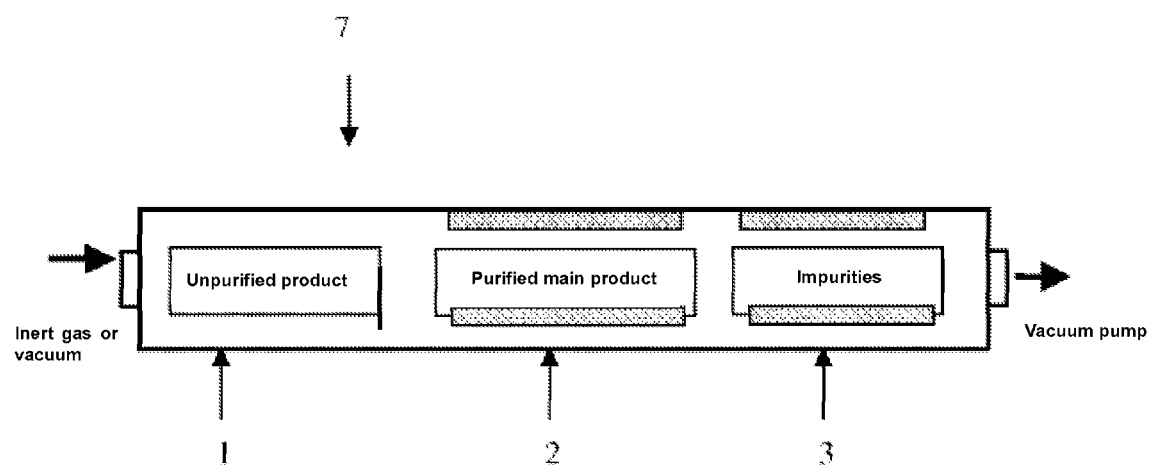
FIG. 1 is a schematic view of the conventional sublimation system for OLED materials.
Figure 2:
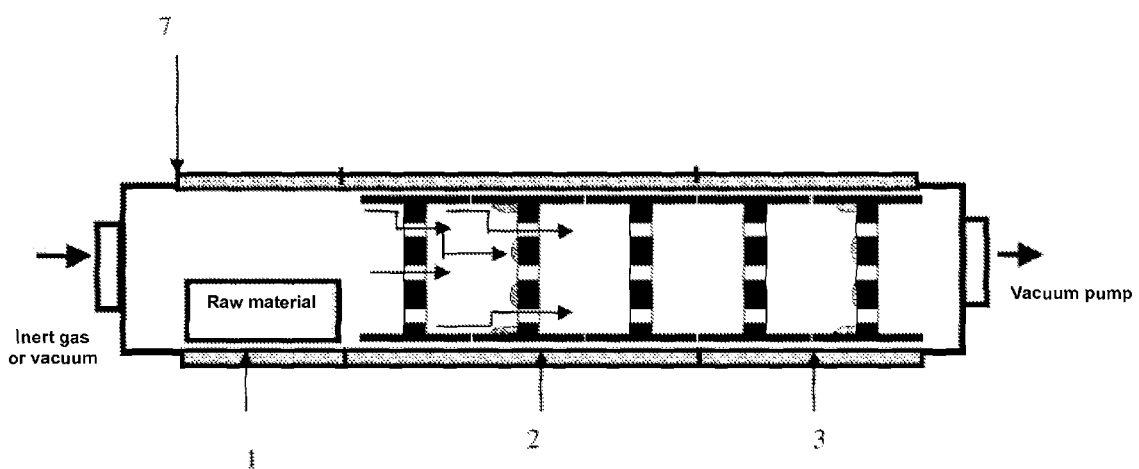
FIG. 2 is a schematic view of the improved sublimation system of this invention.
Figure 3:
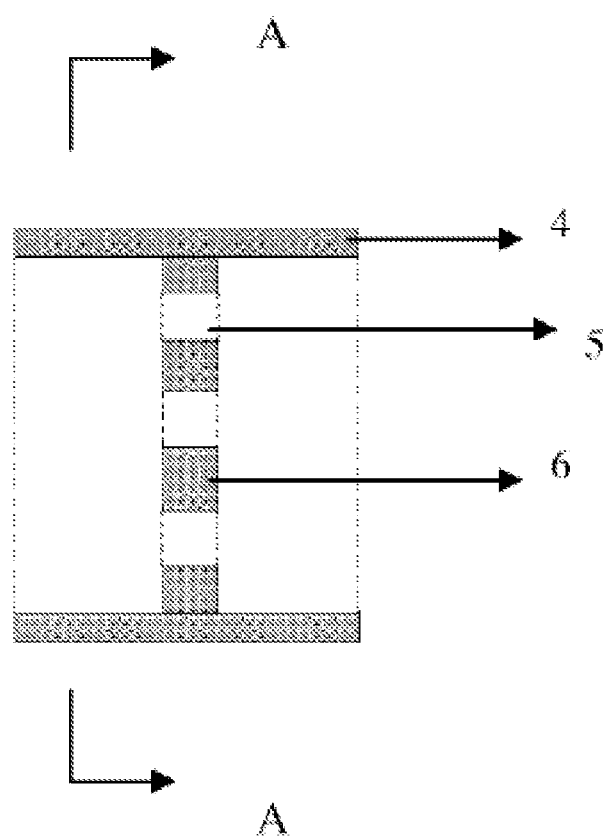
FIG. 3 is a structural view of the collection region of this invention.
Figure 4:
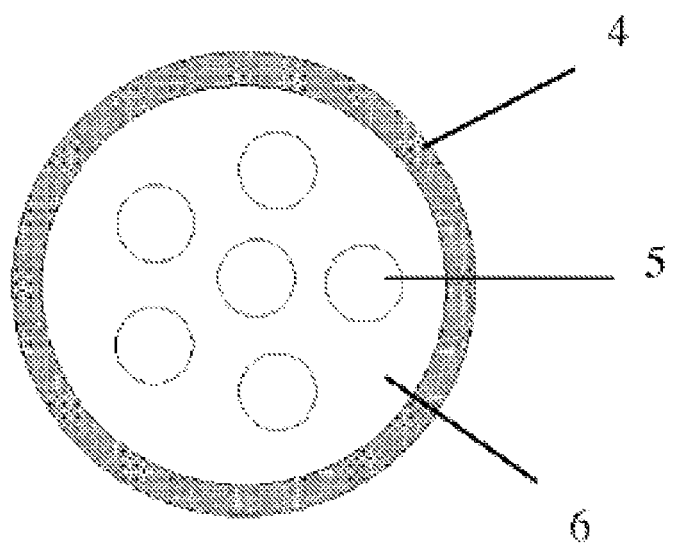
FIG. 4 is a section view along the A-A direction in FIG. 3.

As shown from FIG. 1 to FIG. 4, in the present invention circular plates 6 with through holes 5 are applied in the collection region 2 and the impurity region 3 of a sublimation tube 7. By this means the gas flow is made to go through a zigzagged and prolonged path, and better seperation between the main product and the impurities is expected. For the convenience of product collection, the collection region and the impurity region is composed of a line of space obstruction units. Each unit comprises a hollow cylinder 4 in which is mounted a circular plate 6 having through holes 5. The space barrier in the present invention may be designed to be any other forms, as long as the sublimed gas is made to get through or bypass a more winding path. The circular plate with through holes is a preferred form of the barrier.

Various parameters, such as the number of cylinders, the length of cylinders, the number and size of the through holes, may be adjusted on the basis of the sublimability of the sample.

The difference between the present invention and the conventional sublimation method lies in that several space barrier units are employed in the outer sublimation tube in this invention. Such an alignment of barrier units can promote the separation between the main product and the impurities.

Comparison Experiment:

To verify the superiority of the method in the claimed invention, comparisons were made between the new sublimation technique and the conventional method, by purifying the common OLED material NPB. A sublimation outer tube 7 with a length of 100 cm is adopted, and the raw material to be sublimed is placed about 10 cm from the gas inlet. Argon flow is controlled within a range from 0 to 10 sccm. The degree of vacuum is limited within a range of $1\text{-}9\times10^{-4}$ torr.

In the conventional sublimation system, the purified material is deposited on a wide range of area, and may even overlap with the deposited impurities. For example: NPB has a deposition range of 15 cm to 30 cm in the conventional system. Although most of the impurities are deposited in the impurity region, some of them still extend into the collection region. By using the invented method, NPB was deposited into a much smaller range of 5 cm to 15 cm. And the sublimation yield was found to be increased by 10-20%, while the purity was also improved after being sublimated for the same times.

Detailed results are listed in Table 1

TABLE 1

Comparison of sublimation yields of 10 g of NPB between two systems

|  | Weight of Raw Material | Weight of Purified Product | Yield | Yield Difference |
|---|---|---|---|---|
| Conventional Method | 10 g | 5.8 g | 58% |  |
| Method of the Present invention | 10 g | 7.6 g | 76% |  |
|  |  |  |  | 18% |

Given in Table 2 are the characterization results for purified NPB obtained by different sublimation methods (TGA, Shimadzu/Japan, TGA-50).

TABLE 2

Purity analysis for NPB after one sublimation by different methods

|  | Liquid Chromatographic Purity of Raw Material | Liquid Chromatographic Purity After Sublimation | Thermogravimetic Analysis ° C. (5% loss) |
|---|---|---|---|
| Conventional Method | 99.2% | 99.43% | 386 |
| Method of the Present invention | 99.2% | 99.67% | 395 |

The liquid chromatographic purities and the TGA thermogravimetric results indicated that the method of the present invention improves the purity of NPB. There was a quite small purity difference, but even such a small purity difference of OLED materials would be sufficient to bring significant difference in the device performance.

Figure 5:
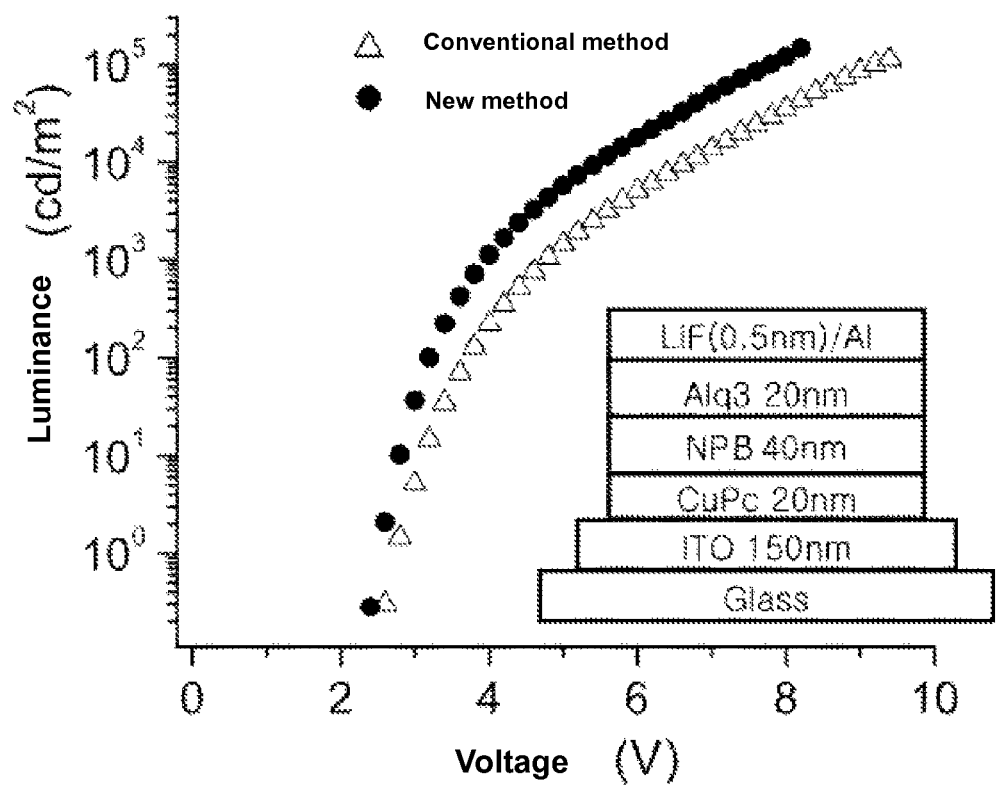
FIG. 5 is a graph comparing the luminance of devices made from materials purified by the conventional sublimation method and the improved method in this invention.

FIG. 5 is the luminance-voltage curve of devices using the hole transport material NPB sublimed by two methods. The devices' performance suggested that the material purified by the new method of the present invention has better charge transport property than the material sublimed by the traditional method. In a device using the material purified by the new method, the threshold voltage was decreased from 5V to 4V under 1000 nit by nearly 1V. It is understood that the impurities in the OLED device are capable to interfere the charge transport, thus by using the purer material sublimed by the invented new method the OLED performance was improved.

Figure 6:
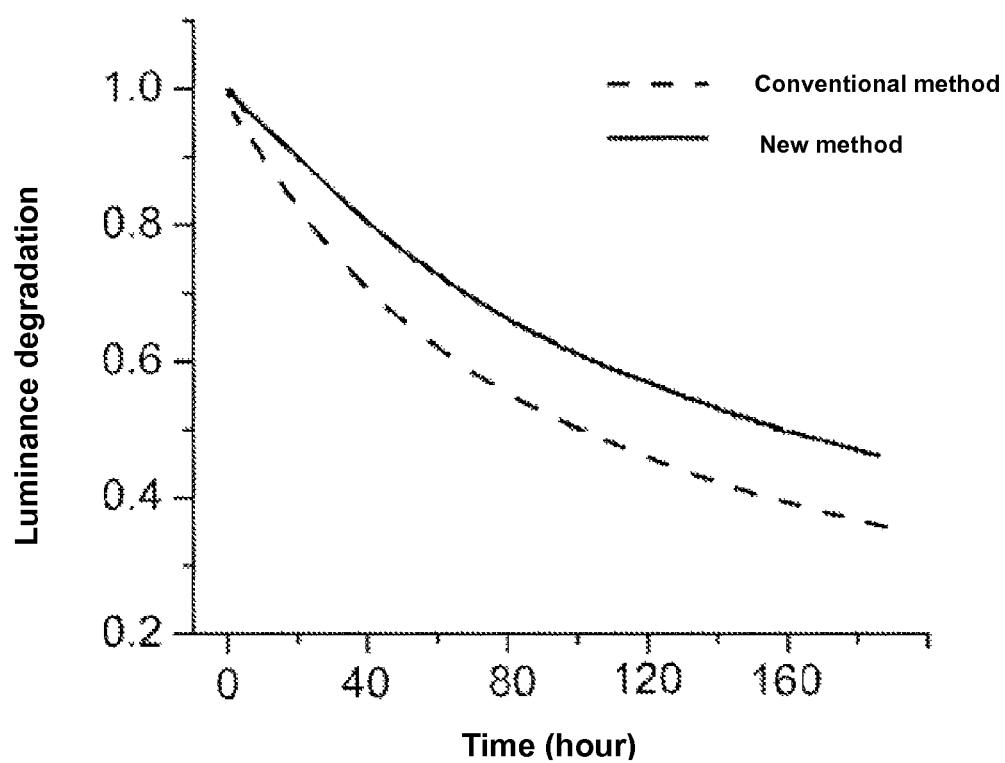
FIG. 6 is a graph comparing the lifetime of devices made from materials purified by the conventional sublimation method and the improved method in this invention, under a constant current density of 50 mA/cm$^2$ The symbols in the drawings are listed as below:
1—heating region, 2—collection region, 3—impurity region, 4—circular cylinder, 5—through hole, 6—circular plate, and 7—sublimation outer tube.

Device lifetime was also compared for OLEDs using materials purified by different methods. FIG. 6 is a lifetime curve showing the luminance degradation under a constant current density of 50 mA/cm$^2$. The degradation curve of the device using the material purified by the new method is less steep than that of the device using material purified by the conventional method, suggesting a longer lifetime for the former one. The principle of OLEDs suggests that the improvement for the performances of such devices is mainly attributed to the increased substance purity. It is therefore proved that the new sublimation method can improve the performances of OLEDs remarkably by elevating the purity level of the sublimed product.

Principle Analysis

The two sublimation techniques differ in that the new method employs space obstruction units in the sublimation tube, so that the sublimed substances have to go through a longer distance before reaching the collection region. A better seperation by the new method increases the sublimation yield and product purity In the conventional method, the sublimed product and the impurities can only condense on the wall of the inner sublimation tube. During the sublimation-condensation process, a few molecules are directly discharged out of the sublimation tube by the vacuum pump, causing material loss. Meanwhile, plenty molecules of the main product condensed beyond the collection region and settle down in the impurity region, as a concequence of limited area of cold surface; or even the impurities may condense in the collection region because of short length of condensation area, causing poor purification effect after sublimation.

The advantage of the new method lies in that the sublimed gas flow is subjected to the interference from the space barrier units, which give the sublimed vapor a prolonged travelling time and increased condensaion surface to achieve better seperation and less material loss. In summary, the new method of the present invention can improve both the yield and the purity of sublimed product.

CONCLUSION

A new sublimation method for the purification of organic small molecules is established by aligning space obstruction units in the conventional sublimation tube. By employing this new method, the sublimation yield has been improved by 10-20%, and the purity of product is also increased compared with the conventional method. As a result of elevated material quality, the OLED performances has been improved simultaneously. For example, the turn-on voltage was decreased by about 1V, and the luminescence lifetime was prolonged by 1.5 times.

The invention claimed is:

1. A sublimation purification method of organic small molecules performed in a system, the method comprising: an organic-small-molecule compound to be sublimed and purified as a main product being placed in the heating region of a sublimation tube, and a vacuum pump being started, a temperature gradient being built up by stepwise heating, the main product being enriched in a collection region adjacent to the heating region and the volatile impurities being enriched in an impurity region between the collection region and the vacuum pump, the sublimation and purification including a gas having the main product and/or impurities passes through or bypasses barriers fastened in the collection region in a zigzagged or prolonged path from the heating region toward the vacuum pump.

2. The method according to claim 1, wherein the barriers are fastened in the impurity region.

3. The method according to claim 1, wherein the barriers are semicircular plates and crosswise fastened and staggered on the inner wall of the collection region.

4. The method according to claim 1, wherein the barriers each are a circular plate with a plurality of through holes, the collection region and/or the impurity region being composed of a plurality of hollow circular cylinders aligned and in close contact with the inner wall of the sublimation tube, a circular plate being fastened in each of the circular cylinder, an angle being formed between the axial direction of the circular cylinder and the plane of the circular plate, and the circular cylinder and the circular plate forming a space obstruction unit.

5. The method according to claim 4, wherein the axial direction of the circular cylinder is perpendicular to the plane of the circular plate.

6. The method according to claim 4, wherein the through holes are uniformly distributed on the circular plate.

7. The method according to claim 2, wherein the barriers are semicircular plates and crosswise fastened and staggered on the inner wall of the collection region.

8. The method according to claim 2, wherein the barriers are each a circular plate with a plurality of through holes, the collection region and/or the impurity region being composed of a plurality of hollow circular cylinders aligned and in close contact with the inner wall of the sublimation tube, a circular plate being fastened in each of the circular cylinder, an angle being formed between the axial direction of the circular cylinder and the plane of the circular plate, and the circular cylinder and the circular plate forming a space obstruction unit.

9. A sublimation purification method of organic small molecules, the method comprising:
placing an organic-small-molecule compound to be sublimed in a heating region of a sublimation tube, the sublimation tube comprising the heating region, a collection region adjacent to the heating region, a impurity region between the collection region and a vacuum pump, and one or more barriers located in the collection region so as to form a zigzagged or prolonged path through the collection region;
starting the vacuum pump;
causing a temperature gradient between the collection region and impurity region to be built up by stepwise heating;
passing gas having a main product and volatile impurities through at least a portion of the zigzagged or prolonged path;
enriching the main product in the collection region of the sublimation tube after passing through at least a portion of the zigzagged or prolonged path; and
enriching the volatile impurities in the impurity region of the sublimation tube after traversing the collection region and passing through at least a portion of the zigzagged or prolonged path.

10. The method according to claim 9, wherein the barriers are also fastened in the impurity region.

11. The method according to claim 9, wherein the barriers are semicircular plates and crosswise fastened and staggered on the inner wall of the collection region.

12. The method according to claim 9, wherein the barriers each include a circular plate with a plurality of through holes, the collection region and/or the impurity region being composed of a plurality of hollow circular cylinders aligned and in close contact with the inner wall of the sublimation tube, a circular plate being fastened in each of the circular cylinder, an angle being formed between the axial direction of the circular cylinder and the plane of the circular plate, and the circular cylinder and the circular plate forming a space obstruction unit.

13. The method according to claim 12, wherein the axial direction of the circular cylinder is perpendicular to the plane of the circular plate.

14. The method according to claim 12, wherein the through holes are uniformly distributed on the circular plate.

15. The method according to claim 10, wherein the barriers are semicircular plates and crosswise fastened and staggered on the inner wall of the collection region.

16. The method according to claim 10, wherein the barriers each include a circular plate with a plurality of through holes, the collection region and/or the impurity region being composed of a plurality of hollow circular cylinders aligned and in close contact with the inner wall of the sublimation tube, a circular plate being fastened in each of the circular cylinder, an angle being formed between the axial direction of the circular cylinder and the plane of the circular plate, and the circular cylinder and the circular plate forming a space obstruction unit.

17. The method of claim 1, further comprising barriers located in the impurity region so as to form a zigzagged or prolonged path through the impurity region.

18. The method of claim 1, further comprising condensing the main product on the barriers located in the collection region.

19. The method of claim 9, further comprising barriers located in the impurity region so as to form a zigzagged or prolonged path through the impurity region.

20. The method of claim 9, further comprising condensing the main product on the barriers located in the collection region.

* * * * *